United States Patent
Whitman

(10) Patent No.: US 12,305,223 B2
(45) Date of Patent: May 20, 2025

(54) METHODS AND PROBES FOR PERFORMING PCR WITH MELT ANALYSIS FOR INCREASED MULTIPLEXING

(71) Applicant: LUMINEX CORPORATION, Austin, TX (US)

(72) Inventor: Doug Whitman, Round Rock, TX (US)

(73) Assignee: LUMINEX CORPORATION, Austin, TX (US)

( * ) Notice: Subject to any disclaimer, the term of this patent is extended or adjusted under 35 U.S.C. 154(b) by 555 days.

(21) Appl. No.: 17/824,215

(22) Filed: May 25, 2022

(65) Prior Publication Data

US 2022/0282307 A1  Sep. 8, 2022

Related U.S. Application Data

(63) Continuation of application No. 16/690,525, filed on Nov. 21, 2019, now Pat. No. 11,371,080.

(60) Provisional application No. 62/773,663, filed on Nov. 30, 2018.

(51) Int. Cl.
  *C12Q 1/6818*  (2018.01)
  *C12Q 1/6876*  (2018.01)

(52) U.S. Cl.
  CPC ......... *C12Q 1/6818* (2013.01); *C12Q 1/6876* (2013.01); *C12Q 2521/101* (2013.01); *C12Q 2525/101* (2013.01); *C12Q 2525/173* (2013.01); *C12Q 2525/186* (2013.01); *C12Q 2525/197* (2013.01); *C12Q 2527/107* (2013.01); *C12Q 2527/143* (2013.01)

(58) Field of Classification Search
  CPC ............ C12Q 1/6818; C12Q 2525/101; C12Q 2525/186; C12Q 2527/107
  See application file for complete search history.

(56) References Cited

U.S. PATENT DOCUMENTS

| | | |
|---|---|---|
| 9,657,332 B2 | 5/2017 | Whitman et al. |
| 9,982,291 B2 | 5/2018 | Johnson et al. |
| 2002/0169562 A1 | 11/2002 | Stephanopoulos et al. |
| 2013/0302794 A1 | 11/2013 | Li et al. |
| 2015/0044680 A1 | 2/2015 | Whitman et al. |
| 2017/0298423 A1 | 10/2017 | Whitman et al. |
| 2018/0073056 A1 | 3/2018 | Kozlov et al. |
| 2018/0073064 A1 | 5/2018 | Kozlov et al. |
| 2020/0199658 A1 | 6/2020 | Whitman et al. |

FOREIGN PATENT DOCUMENTS

WO  WO 2016/101959  6/2016

OTHER PUBLICATIONS

Faltin et al. Current Methods for Fluorescence-Based Universal Sequence-Dependent Detection of Nucleic Acids in Homogeneous Assays and Clinical Applications. Clinical Chemistry 59(11)1567-1582. (Year: 2013).*
Office Action issued in U.S. Appl. No. 16/690,525, mailed Oct. 8, 2021.

* cited by examiner

*Primary Examiner* — Samuel C Woolwine
(74) *Attorney, Agent, or Firm* — Parker Highlander PLLC

(57) ABSTRACT

Methods and compositions for the detection and quantification of nucleic acids are provided. In certain embodiments, methods involve the use of cleavable probes capable of forming double-stranded structures, such as hairpin structures, which probes can be distinguished from one another on the basis of reporter signal, melt properties, or both.

13 Claims, 7 Drawing Sheets

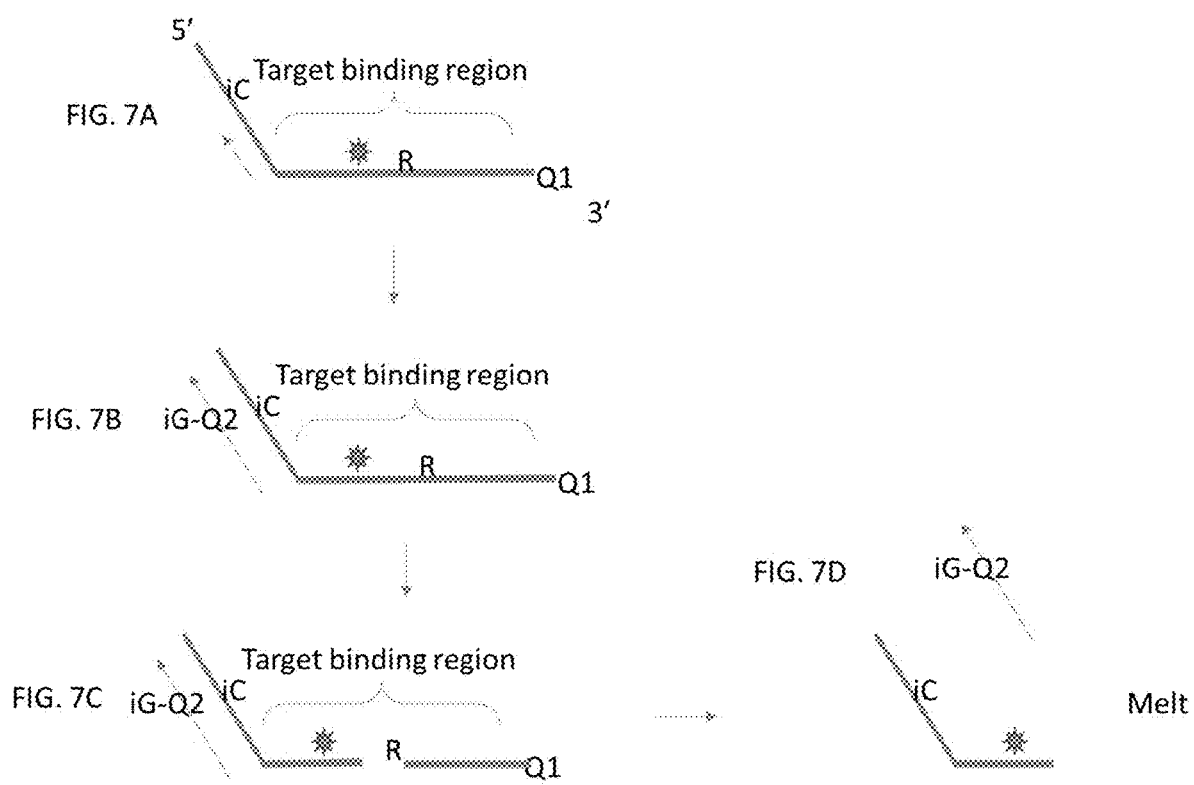
FIG. 7A-D

METHODS AND PROBES FOR PERFORMING PCR WITH MELT ANALYSIS FOR INCREASED MULTIPLEXING

This application is continuation of U.S. patent application Ser. No. 16/690,525, filed Nov. 21, 2019, which claims the benefit of U.S. Provisional Patent Application No. 62/773,663, filed Nov. 30, 2018, the entirety of which is incorporated herein by reference.

BACKGROUND OF THE INVENTION

1. Field of the Invention

The present invention relates generally to the field of molecular biology. More particularly, it concerns the detection of nucleic acids.

2. Description of Related Art

Polymerase chain reaction (PCR) is a molecular biology technique for enzymatically replicating DNA without using a living organism. PCR is commonly used in medical and biological research labs for a variety of tasks, such as the detection of hereditary diseases, the identification of genetic fingerprints, and the diagnosis of infectious diseases. PCR has been accepted by molecular biologists as the method of choice for nucleic acid detection because of its unparalleled amplification and precision capability. Detection of amplification products can be performed in real time or at the end-point of the PCR reaction.

Several assay chemistries have been used in PCR detection methods. These assay chemistries include using double-stranded DNA binding dyes and dual-labeled oligonucleotides, such as hairpin primers, and hairpin probes. However, a drawback of these chemistries is limited multiplexing capability due to the need for spectrally distinct fluorochromes (and instrumentation with multiple emission sources, detectors, and filters to detect the multiple spectrally distinct fluorochromes) for each assay within a multiplex reaction. Technologies have been proposed that incorporate a melt analysis to increase the number of targets that can be detected per fluorochrome. Examples of which are disclosed in U.S. Pat. Nos. 9,982,291, 9,657,332, U.S. 2018/0073056; U.S. 2018/0073064; and WO/2016/101959, each of which is incorporated herein by reference. While these technologies may increase the multiplexing of certain PCR reactions, they have drawbacks in terms of the complexity of designing suitable probes/primers and/or limitations on range of melt temperatures that can be achieved.

SUMMARY OF THE INVENTION

The present invention relates to systems and methods for amplification and detection of DNA. In particular, embodiments of the present invention provide systems and methods that greatly increase multiplexing capabilities of detectable probes for use in detecting amplified target sequences.

In a first embodiment, a probe for detecting the presence of a target nucleic acid is provided, the probe comprising, from 5' to 3': (a) a target-specific region comprising a first nucleotide sequence complementary to a target nucleotide sequence, a quencher, and a reporter, wherein the quencher is coupled to the target-specific region at a first location that is 5' relative to the reporter, the reporter is coupled to the target-specific region at a second location that is 3' relative to the quencher, and the first location and the second location are separated by a distance sufficient to permit cleavage of quencher but not the reporter; (b) a polymerase extension-blocking moiety; (c) a melt-signature region comprising a second nucleotide sequence that is not complementary to the target nucleotide sequence and includes at least one non-naturally occurring nucleotide; (d) a loop region; and (e) a melt-signature complementary region comprising a third nucleotide sequence that is complementary to a portion of the second nucleotide sequence. In certain embodiments, the first nucleotide sequence comprises from 4 to 40 contiguous nucleotides, 5 to 36 contiguous nucleotides, or 20 to 36 contiguous nucleotides. In some embodiments, the quencher is coupled to the 5'-most nucleotide of the first nucleotide sequence. In some embodiments, the first location and the second location are separated by at least 5, 6, 7, 8, 9, or 10 nucleotides of the first nucleotide sequence. In certain embodiments, the third nucleotide sequence is complementary to from 5 to 35 nucleotides, 6 to 26 nucleotides, or 10 to 36 nucleotides of the second nucleotide sequence.

Another embodiment provides a method for detecting the presence of a target nucleic acid comprising: (a) contacting a sample with a first primer comprising a first nucleotide sequence complementary to a first portion of the target nucleotide sequence and a probe, the probe comprising, from 5' to 3', (i) a target-specific region comprising a second nucleotide sequence, wherein the second nucleotide sequence is complementary to a second portion of the target nucleotide sequence, wherein the second portion of the target nucleotide sequence is located downstream of the first portion, wherein the second nucleotide sequence is labelled with a first quencher and a reporter, and wherein the first quencher is located 5' relative to the reporter; (ii) a polymerase extension-blocking moiety; (iii) a melt-signature region comprising a third nucleotide sequence, wherein the third nucleotide sequence is not complementary to the target nucleotide sequence, and wherein the third nucleotide sequence includes a first non-naturally occurring nucleotide; (iii) a loop region; and (iv) a melt-signature complementary region comprising a fourth nucleotide sequence, wherein the forth nucleotide sequence is complementary to a portion of the third nucleotide sequence; (b) hybridizing the melt-signature region with the melt-signature complementary region to form a first hairpin structure having a first melting temperature; (c) extending the melt-signature complementary region along the melt-signature region using a polymerase to form a second hairpin structure having a second melting temperature, wherein during the extending the polymerase incorporates a second non-naturally occurring nucleotide into the second hairpin structure that is complementary to the first non-naturally occurring nucleotide, wherein the second non-naturally occurring nucleotide is labelled with a second quencher, and wherein the second melting temperature is higher than the first melting temperature; (d) hybridizing the first primer to the first portion of the target nucleotide sequence and hybridizing the probe to the second portion of the target nucleotide sequence if the target nucleotide is present in the sample; (e) extending the first primer along the target nucleotide sequence using a polymerase having 5' nuclease activity to partially cleave the target-specific region of the probe, wherein the partial cleaving cleaves a portion of the probe labelled with the first quencher and does not cleave a portion of the probe labelled with the reporter; (f) taking a measurement of a reporter signal at at least a first temperature that is below the second melting temperature and a measurement of a reporter signal at at least a second temperature that is above the second melting temperature; and (d) detecting the presence of the target nucleic acid if there is a change in the reporter signal measured below the second melting temperature as compared to the reporter signal measured above the second melting temperature indicative of the absence of the first quencher from the second hairpin structure as a result of the partial cleavage of the target-specific region of the probe. In certain embodiments, the second melting temperature is 75° Celsius or higher. In certain embodiments, the second melting temperature is a temperature between 75° Celsius and 90° Celsius.

Another embodiment provides a method for detecting the presence of a target nucleic acid comprising: (a) contacting a sample with: a pair of primers configured to hybridize to opposite strands of the target nucleotide sequence; and a probe, the probe comprising, from 5' to 3', (i) a target-specific region comprising a first nucleotide sequence, wherein the first nucleotide sequence is complementary to a portion of the target nucleotide sequence bounded by the primer pair, wherein the first nucleotide sequence is labelled with a first quencher and a reporter, and wherein the first quencher is located 5' relative to the reporter; (ii) a polymerase extension-blocking moiety; (iii) a melt-signature region comprising a second nucleotide sequence, wherein the second nucleotide sequence is not complementary to the target nucleotide sequence, and wherein the second nucleotide sequence includes a first non-naturally occurring nucleotide; (iii) a loop region; and (iv) a melt-signature complementary region comprising a third nucleotide sequence, wherein the third nucleotide sequence is complementary to a portion of the second nucleotide sequence; (b) hybridizing the melt-signature region with the melt-signature complementary region to form a first hairpin structure having a first melting temperature; (c) extending the melt-signature complementary region along the melt-signature region using a polymerase to form a second hairpin structure having a second melting temperature, wherein during the extending the polymerase incorporates a second non-naturally occurring nucleotide into the second hairpin structure that is complementary to the first non-naturally occurring nucleotide, wherein the second non-naturally occurring nucleotide is labelled with a second quencher, and wherein the second melting temperature is higher than the first melting temperature; (d) hybridizing the primer pair to the opposite strands of the target nucleotide sequence and hybridizing the probe to the first portion of the target nucleotide sequence, if the target nucleotide is present in the sample; (e) extending the primer pair along the opposite strands of the target nucleotide sequence using a polymerase having 5' nuclease activity to partially cleave the target-specific region of the probe, wherein the partial cleaving cleaves a portion of the probe labelled with the first quencher and does not cleave a portion of the probe labelled with the reporter; (f) taking a measurement of a reporter signal at at least a first temperature that is below the second melting temperature and a measurement of a reporter signal at at least a second temperature that is above the second melting temperature; and (g) detecting the presence of the target nucleic acid if there is a change in the reporter signal measured below the second melting temperature as compared to the reporter signal measured above the second melting temperature indicative of the absence of the first quencher from the second hairpin structure as a result of the partial cleavage of the target-specific region of the probe. In certain embodiments, the second melting temperature is 75° Celsius or higher. In certain embodiments, the second melting temperature is a temperature between 75° Celsius and 90° Celsius. In certain embodiments of the method, steps (d) and (e) are performed after steps (b) and (c). In other embodiments of the method, steps (d) and (e) are performed before steps (b) and (c). In some embodiments, the method comprises repeating steps (b) through (f) through multiple PCR cycles. In certain aspects, the method comprises repeating steps (d) and (e) through multiple PCR cycles prior to performing steps (b), (c), (f), and (g).

The methods disclosed herein are well-suited to multiplexing. For example, the presence of two or more target nucleic acids may be detected by a method comprising: (a) contacting a sample with: a first pair of primers configured to hybridize to opposite strands of a first target nucleotide sequence; a second pair of primers configured to hybridize to opposite strands of a second target nucleotide sequence; a first probe, the first probe comprising, from 5' to 3', (i) a target-specific region comprising a first nucleotide sequence, wherein the first nucleotide sequence is complementary to a portion of the first target nucleotide sequence bounded by the first primer pair, wherein the first nucleotide sequence is labelled with a first quencher and a reporter, and wherein the first quencher is located 5' relative to the reporter; (ii) a polymerase extension-blocking moiety; (iii) a melt-signature region comprising a second nucleotide sequence, wherein the second nucleotide sequence is not complementary to the first target nucleotide sequence, and wherein the second nucleotide sequence includes a first non-naturally occurring nucleotide; (iii) a loop region; and (iv) a melt-signature complementary region comprising a third nucleotide sequence, wherein the third nucleotide sequence is complementary to a portion of the second nucleotide sequence; and a second probe, the second probe comprising, from 5' to 3', (i) a target-specific region comprising a first nucleotide sequence, wherein the first nucleotide sequence is complementary to a portion of the second target nucleotide sequence bounded by the second primer pair, wherein the first nucleotide sequence is labelled with a first quencher and a reporter, and wherein the first quencher is located 5' relative to the reporter; (ii) a polymerase extension-blocking moiety; (iii) a melt-signature region comprising a second nucleotide sequence, wherein the second nucleotide sequence is not complementary to the first target nucleotide sequence, and wherein the second nucleotide sequence includes a first non-naturally occurring nucleotide; (iii) a loop region; and (iv) a melt-signature complementary region comprising a third nucleotide sequence, wherein the third nucleotide sequence is complementary to a portion of the second nucleotide sequence; (b) hybridizing the melt-signature region of the first probe with the melt-signature complementary region of the first probe to form a first hairpin structure having a first melting temperature, and hybridizing the melt-signature region of the second probe with the melt-signature complementary region of the second probe to form a second hairpin structure having a second melting temperature; (c) extending the melt-signature complementary region of the first probe along the melt-signature region of the first probe using a polymerase to form a third hairpin structure having a third melting temperature, and extending the melt-signature complementary region of the second probe along the melt-signature region of the second probe using a polymerase to form a fourth hairpin structure having a fourth melting temperature, wherein during the extending of the melt-signature complementary regions of each of the first and second probes the polymerase incorporates a second non-naturally occurring nucleotide labelled with a second quencher into each of the third and fourth hairpin structures that is complementary to the first non-naturally occurring nucleotide, and wherein the third melting temperature is higher than the first melting temperature, the fourth melting temperature is higher than the second melting temperature, and the third melting temperature is different from the fourth melting temperature; (d) amplifying the first and second target nucleotides, if present in the sample, by polymerase chain reaction (PCR) using a polymerase having 5' to 3' nuclease activity such that during an extension step of each PCR cycle, the 5' to 3' nuclease activity of the polymerase partially cleaves the target-specific regions of the first and second probes, wherein the partial cleaving cleaves a portion of each of the first and second probes labelled with the first quencher and does not cleave a portion of the first and second probes labelled with the reporter; (e) measuring a reporter signal at at least a first temperature that is below the third and fourth melting temperatures, measuring a reporter signal at at least a second temperature that is above the third melting temperature, and measuring a reporter signal at at least a third temperature that is above the fourth melting temperature; and (f) detecting the presence of the first target nucleic acid if there is a change in the reporter signal measured below the third melting temperature as compared to the reporter signal measured above the third melting temperature indicative of the absence of the first quencher from the third hairpin structure as a result of the partial cleavage of the target-specific region of the first probe, and detecting the presence of the second target nucleic acid if there is a change in the reporter signal measured below the fourth melting temperature as compared to the reporter signal measured above the fourth melting temperature indicative of the absence of the first quencher from the fourth hairpin structure as a result of the partial cleavage of the target-specific region of the second probe. In certain embodiments, the third melting temperature, the fourth melting temperature, or both, is 75° Celsius or higher. In certain embodiments, the third melting temperature, the fourth melting temperature, or both, is a temperature between 75° Celsius and 90° Celsius. In certain embodiments of the method, the measuring of step (e) is repeated a plurality of times during the amplifying of step (d) in order to monitor the PCR in real time. In other embodiments, the measuring of step (e) is performed only after the amplifying of step (d) has reached a plateau phase.

Another embodiment provides a probe for detecting the presence of a target nucleic acid, the probe comprising, from 5' to 3': (a) a target-specific region comprising a first nucleotide sequence complementary to a target nucleotide sequence, a quencher, a reporter, and a ribobase, wherein the quencher is coupled to the target-specific region at a first location that is 5' relative to the reporter, the reporter is coupled to the target-specific region at a second location that is 3' relative to the quencher, and the ribobase is positioned such that cleavage of the probe by a ribonuclease would cleave the probe between the first location and the second location of the first nucleotide sequence; (b) a polymerase extension-blocking moiety; (c) a melt-signature region comprising a second nucleotide sequence that is not complementary to the target nucleotide sequence and includes at least one non-naturally occurring nucleotide; (d) a loop region; and (e) a melt-signature complementary region comprising a third nucleotide sequence that is complementary to a portion of the second nucleotide sequence. In certain embodiments, the first nucleotide sequence comprises from 4 to 40 contiguous nucleotides, 5 to 36 contiguous nucleotides, or 20 to 36 contiguous nucleotides. In some embodiments, the quencher is coupled to the 5'-most nucleotide of the first nucleotide sequence. In some embodiments, the first location and the second location are separated by at least 2, 3, 4, 5, 6, 7, 8, 9, or 10 nucleotides of the first nucleotide sequence. In certain embodiments, the third nucleotide sequence is complementary to from 5 to 35 nucleotides, 6 to 26 nucleotides, or 10 to 36 nucleotides of the second nucleotide sequence.

In one embodiment, a method is provided for detecting the presence of a target nucleic acid comprising: (a) contacting a sample with a probe, the probe comprising, from 5' to 3', (i) a target-specific region comprising a first nucleotide sequence, wherein the first nucleotide sequence is complementary to a portion of the target nucleotide sequence, wherein the first nucleotide sequence comprises a ribobase, wherein the first nucleotide sequence is labelled with a first quencher and a reporter, and wherein the first quencher is located 5' relative to the reporter; (ii) a polymerase extension-blocking moiety; (iii) a melt-signature region comprising a second nucleotide sequence, wherein the second nucleotide sequence is not complementary to the target nucleotide sequence, and wherein the second nucleotide sequence includes a first non-naturally occurring nucleotide; (iii) a loop region; and (iv) a melt-signature complementary region comprising a third nucleotide sequence, wherein the third nucleotide sequence is complementary to a portion of the second nucleotide sequence; (b) hybridizing the melt-signature region with the melt-signature complementary region to form a first hairpin structure having a first melting temperature; (c) extending the melt-signature complementary region along the melt-signature region using a polymerase to form a second hairpin structure having a second melting temperature, wherein during the extending the polymerase incorporates a second non-naturally occurring nucleotide into the second hairpin structure that is complementary to the first non-naturally occurring nucleotide, wherein the second non-naturally occurring nucleotide is labelled with a second quencher, and wherein the second melting temperature is higher than the first melting temperature; (d) hybridizing the probe to the second portion of the target nucleotide sequence if the target nucleotide is present in the sample; (e) contacting the hybridized probe with an endoribonuclease to cleave the target-specific region of the probe, wherein the probe is cleaved between the first quencher and the reporter; (f) taking a measurement of a reporter signal at at least a first temperature that is below the second melting temperature and a measurement of a reporter signal at at least a second temperature that is above the second melting temperature; and (g) detecting the presence of the target nucleic acid if there is a change in the reporter signal measured below the second melting temperature as compared to the reporter signal measured above the second melting temperature indicative of the absence of the first quencher from the second hairpin structure as a result of the partial cleavage of the target-specific region of the probe. In certain embodiments, the second melting temperature is 75° Celsius or higher. In certain embodiments, the second melting temperature is a temperature between 75° Celsius and 90° Celsius.

Another embodiment provides a method for detecting the presence of a target nucleic acid comprising: (a) contacting a sample with: a pair of primers configured to hybridize to opposite strands of the target nucleotide sequence; and a probe, the probe comprising, from 5' to 3', (i) a target-specific region comprising a first nucleotide sequence, wherein the first nucleotide sequence is complementary to a portion of the target nucleotide sequence bounded by the primer pair, wherein the first nucleotide sequence is labelled with a first quencher and a reporter, wherein the first quencher is located 5' relative to the reporter, and wherein the first nucleotide sequence comprises a ribobase located between the quencher and the reporter; (ii) a polymerase extension-blocking moiety; (iii) a melt-signature region comprising a second nucleotide sequence, wherein the second nucleotide sequence is not complementary to the target nucleotide sequence, and wherein the second nucleotide sequence includes a first non-naturally occurring nucleotide; (iii) a loop region; and (iv) a melt-signature complementary region comprising a third nucleotide sequence, wherein the third nucleotide sequence is complementary to a portion of the second nucleotide sequence; (b) hybridizing the melt-signature region with the melt-signature complementary region to form a first hairpin structure having a first melting temperature; (c) extending the melt-signature complementary region along the melt-signature region using a polymerase to form a second hairpin structure having a second melting temperature, wherein during the extending the polymerase incorporates a second non-naturally occurring nucleotide into the second hairpin structure that is complementary to the first non-naturally occurring nucleotide, wherein the second non-naturally occurring nucleotide is labelled with a second quencher, and wherein the second melting temperature is higher than the first melting temperature; (d) hybridizing the primer pair to the opposite strands of the target nucleotide sequence and hybridizing the probe to the first portion of the target nucleotide sequence, if the target nucleotide is present in the sample; (e) contacting the hybridized probe with an endoribonuclease to cleave the target-specific region of the probe, wherein the probe is cleaved between the first quencher and the reporter, and wherein the cleaved probe comprising the reporter is no longer hybridized to the target nucleotide sequence; (f) extending the primer pair along the opposite strands of the target nucleotide sequence using a polymerase; (g) taking a measurement of a reporter signal at at least a first temperature that is below the second melting temperature and a measurement of a reporter signal at at least a second temperature that is above the second melting temperature; and (h) detecting the presence of the target nucleic acid if there is a change in the reporter signal measured below the second melting temperature as compared to the reporter signal measured above the second melting temperature indicative of the absence of the first quencher from the second hairpin structure as a result of the partial cleavage of the target-specific region of the probe. In certain embodiments, the second melting temperature is 75° Celsius or higher. In certain embodiments, the second melting temperature is a temperature between 75° Celsius and 90° Celsius. In some embodiments of the method, steps (d) to (f) are performed after steps (b) and (c). In other embodiments of the method, steps (d) to (f) are performed before steps (b) and (c). In certain embodiments, the method comprises repeating steps (b) through (g) through multiple PCR cycles. In some embodiments, the method comprises repeating steps (d) to (f) through multiple PCR cycles prior to performing steps (b), (c), (g), and (h).

In another embodiment, a method is provided for detecting the presence of two or more target nucleic acids comprising: (a) contacting a sample with: a first pair of primers configured to hybridize to opposite strands of a first target nucleotide sequence; a second pair of primers configured to hybridize to opposite strands of a second target nucleotide sequence; a first probe, the first probe comprising, from 5' to 3', (i) a target-specific region comprising a first nucleotide sequence, wherein the first nucleotide sequence is complementary to a portion of the first target nucleotide sequence bounded by the first primer pair, wherein the first nucleotide sequence is labelled with a first quencher and a reporter, wherein the first quencher is located 5' relative to the reporter, and wherein the first nucleotide sequence comprises a ribobase positioned such that cleavage of the probe by an endoribonuclease would cleave the probe between the first quencher and the reporter; (ii) a polymerase extension-blocking moiety; (iii) a melt-signature region comprising a second nucleotide sequence, wherein the second nucleotide sequence is not complementary to the first target nucleotide sequence, and wherein the second nucleotide sequence includes a first non-naturally occurring nucleotide; (iii) a loop region; and (iv) a melt-signature complementary region comprising a third nucleotide sequence, wherein the third nucleotide sequence is complementary to a portion of the second nucleotide sequence; and a second probe, the second probe comprising, from 5' to 3', (i) a target-specific region comprising a first nucleotide sequence, wherein the first nucleotide sequence is complementary to a portion of the second target nucleotide sequence bounded by the second primer pair, wherein the first nucleotide sequence is labelled with a first quencher and a reporter, wherein the first quencher is located 5' relative to the reporter, and wherein the first nucleotide sequence comprises a ribobase positioned such that cleavage of the probe by an endoribonuclease would cleave the probe between the first quencher and the reporter; (ii) a polymerase extension-blocking moiety; (iii) a melt-signature region comprising a second nucleotide sequence, wherein the second nucleotide sequence is not complementary to the first target nucleotide sequence, and wherein the second nucleotide sequence includes a first non-naturally occurring nucleotide; (iii) a loop region; and (iv) a melt-signature complementary region comprising a third nucleotide sequence, wherein the third nucleotide sequence is complementary to a portion of the second nucleotide sequence; (b) hybridizing the melt-signature region of the first probe with the melt-signature complementary region of the first probe to form a first hairpin structure having a first melting temperature, and hybridizing the melt-signature region of the second probe with the melt-signature complementary region of the second probe to form a second hairpin structure having a second melting temperature; (c) extending the melt-signature complementary region of the first probe along the melt-signature region of the first probe using a polymerase to form a third hairpin structure having a third melting temperature, and extending the melt-signature complementary region of the second probe along the melt-signature region of the second probe using a polymerase to form a fourth hairpin structure having a fourth melting temperature, wherein during the extending of the melt-signature complementary regions of each of the first and second probes the polymerase incorporates a second non-naturally occurring nucleotide labelled with a second quencher into each of the third and fourth hairpin structures that is complementary to the first non-naturally occurring nucleotide, and wherein the third melting temperature is higher than the first melting temperature, the fourth melting temperature is higher than the second melting temperature, and the third melting temperature is different from the fourth melting temperature; (d) amplifying the first and second target nucleotides, if present in the sample, by polymerase chain reaction (PCR); (e) contacting the first and second probes during an annealing or extension phase of the PCR with an endoribonuclease to cleave the target-specific regions of the first and second probes, wherein the first and second probes are cleaved between the first quencher and the reporter, and wherein the cleaved first and second probes comprising the reporter are no longer hybridized to the first and second target nucleotide sequences; (f) measuring a reporter signal at at least a first temperature that is below the third and fourth melting temperatures, measuring a reporter signal at at least a second temperature that is above the third melting temperature, and measuring a reporter signal at at least a third temperature that is above the fourth melting temperature; and (g) detecting the presence of the first target nucleic acid if there is a change in the reporter signal measured below the third melting temperature as compared to the reporter signal measured above the third melting temperature indicative of the absence of the first quencher from the third hairpin structure as a result of the partial cleavage of the target-specific region of the first probe, and detecting the presence of the second target nucleic acid if there is a change in the reporter signal measured below the fourth melting temperature as compared to the reporter signal measured above the fourth melting temperature indicative of the absence of the first quencher from the fourth hairpin structure as a result of the partial cleavage of the target-specific region of the second probe. In certain embodiments, the third melting temperature, the fourth melting temperature, or both, is 75° Celsius or higher. In certain embodiments, the third melting temperature, the fourth melting temperature, or both, is a temperature between 75° Celsius and 90° Celsius. In some embodiments, the measuring of step (f) is repeated a plurality of times during the amplifying of step (d) in order to monitor the PCR in real time. In other embodiments, the measuring of step (f) is performed only after the amplifying of step (d) has reached a plateau phase.

A further embodiment provides a probe for detecting the presence of a target nucleic acid, the probe comprising: (a) a target-specific region comprising a first nucleotide sequence complementary to a target nucleotide sequence; (b) a first stem-forming region having a second nucleotide sequence and located 5' of the target specific region; (c) a loop region located 5' of the first stem forming region; (d) a second stem-forming region having a third nucleotide sequence and located 5' of the stem-forming region, wherein the third nucleotide region is a reverse complement of the second nucleotide sequence; and (e) a labelled region comprising a fourth nucleotide sequence that is not complementary to the target nucleotide sequence and that comprises a labelled, non-naturally occurring nucleotide.

A method is also provided for detecting the presence of a target nucleic acid comprising: (a) contacting a sample with a probe according to the preceding paragraph and a first primer comprising a first nucleotide sequence complementary to a first portion of the target nucleotide sequence; (b) hybridizing the first primer to the first portion of the target nucleotide sequence and hybridizing the probe to a second portion of the target nucleotide sequence if the target nucleotide is present in the sample; (c) extending the first primer along the target nucleotide sequence using a polymerase having 5' nuclease activity to at least partially cleave the target-specific region of the probe to from a truncated probe comprising the first stem-forming region, the loop region, the second stem-forming region, and the labelled region; (d) hybridizing the first stem-forming region of the truncated probe with the second stem-forming region of the truncated probe to form a first hairpin structure having a first melting temperature; (e) extending the second stem-forming region along the first stem-forming region using a polymerase to form a second hairpin structure having a second melting temperature, wherein during the extending the polymerase incorporates a second labelled, non-naturally occurring nucleotide into the second hairpin structure that is complementary to the labelled, non-naturally occurring nucleotide of the labelled region, wherein one of the second labelled, non-naturally occurring nucleotide the labelled, non-naturally occurring nucleotide of the labelled region is labelled with a quencher and the other is labelled with a reporter, and wherein the second melting temperature is higher than the first melting temperature; (f) taking a measurement of a reporter signal at at least a first temperature that is below the second melting temperature and a measurement of a reporter signal at at least a second temperature that is above the second melting temperature; and (g) detecting the presence of the target nucleic acid if there is a change in the reporter signal measured below the second melting temperature as compared to the reporter signal measured above the second melting temperature. In certain embodiments, the second melting temperature is 75° Celsius or higher. In certain embodiments, the second melting temperature is a temperature between 75° Celsius and 90° Celsius. The method may further comprise contacting the sample a second primer, wherein the first primer and the second primer are a pair of primers configured to hybridize to opposite strands of the target nucleotide sequence, and wherein the target-specific region of the probe is complementary to a portion of the target nucleotide sequence bounded by the primer pair; and performing multiple polymerase chain reaction (PCR) cycles.

The various probes described herein may be combined to provide compositions or kits containing a plurality of different probes, each of which may be distinguishable from other probes by its reporter, its melt temperature, or both. For example, one embodiment provides a composition comprising at least a first and a second probe, wherein the reporter of the first probe is identical to the reporter of the second probe, wherein the target-specific region of the first probe has a sequence that is different from the target-specific region of the second probe, and wherein the melt-signature region or hairpin forming region of the first probe has a length and/or GC-content that is different from the length and/or GC-content of the melt-signature region or hairpin forming region of the second probe. The various different probes may comprise or be modified over the course of a reaction to have hairpins or other double-stranded structures with distinguishable melt points (e.g., melt points that differ by 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30° C. from one another, or any range derivable therein).

The various methods disclosed herein may be performed on a sample that is divided into a plurality of partitions or compartments such that if the target nucleic acid is present in the sample, at least one partition of the plurality of partitions or compartments will not contain a target nucleic acid.

Various embodiments of probes disclosed herein comprise a loop region. The loop region may comprise, for example, nucleotides and or a carbon spacer. For example, in some aspects, the loop region may comprise 4-20, 6-15 or 10-15 nucleotides. In certain aspects, the loop region may comprise at least 3-8 consecutive Adenine (A) nucleotides. As a further example, the loop region may comprise a carbon spacer. Carbon spacers may include spacers that may be 3 to 36 carbon atoms in length. Common examples of internal oligonucleotide carbon spacers include spacers that are 3, 9, and 18 carbon atoms in length (i.e., C3, C9, and C18 spacers).

Various embodiments of probes disclosed herein comprise polymerase extension blocking moieties. Examples of extension blocking moieties include carbon spacers. Other polymerase extension blocking moieties may include non-natural nucleotides, ribonucleotides, or any other non-nucleotide chemical moiety.

Certain probe embodiments disclosed herein comprise a ribobase(s). In certain aspects, such a cleavable probe may comprise a sequence comprising 1 to 5 ribonucleotide bases complementary to the target sequence. In some aspects, the cleavable probe may comprise a sequence comprising 3 to 5 ribonucleotide bases that is complimentary to the target nucleic sequence.

Certain aspects of the embodiments concern the use of at least one non-natural nucleotide. In some aspects, the non-natural nucleotide is an isobase, such as iso-guanine (isoG) or iso-cytosine (isoC). In certain aspects, the at least one non-natural nucleotide or the quencher-labeled non-natural nucleotide may be isoG and the other may be isoC.

The methods disclosed herein may be performed as singleplex or multiplex methods. A multiplex method according to the embodiments can comprise the use of at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36 or more distinct probes, or any range derivable therein, wherein each probe comprises either (1) a distinguishable melt point and/or (2) a distinguishable label, such that the signal from each distinct probe may be individually discerned.

In some aspects, a method of the embodiments may further comprise performing multiple polymerase chain reaction cycles. In some aspects, detecting the change in signal from the label comprises detecting the signal before, during, or after performing the multiple polymerase chain reaction cycles. In another aspect, detecting the change in signal from the label comprises detecting the signal only after performing the multiple polymerase chain reaction cycles. In this aspect, the method may further comprise comparing the detected signal from the label to a predetermined ratio of the signal of the label to a reference signal from a label on a non-hybridizing probe.

In some aspects, a method of the embodiments may further comprise quantifying the amount of the target nucleic acid in the sample. For example, quantifying the amount of the target nucleic acid in the sample may comprise: using a standard curve; determining a relative amount of the nucleic acid target; using end-point quantitation; digital PCR quantitation, or determining an amount of the nucleic acid target by relating the PCR cycle number at which the signal is detectable over background to the amount of target present.

In various aspects of the present methods, detecting a change in signal from the reporter may comprise detecting the change (or rate of change) in signal, such as unquenching of a signal when the sample is raised to a higher temperature. In one aspect, the temperature of the sample may be increased above (or decreased below) the melt point of the one or more probes in the sample. In the case where two or more probes are present, changing the temperature of a sample may comprise increasing the temperature of the sample from a temperature that is below the melt point of the two or more probes to a temperature that is above the melt point of the two or more probes. In such a scenario, a reporter signal may be measured at least once at a temperature that is below the melt point of the two or more probes, at least once at a temperature that is above the melt point of the two or more probes, and at least once at a temperature that is between the melt points of the two or more probes.

Various probes, compositions, and methods disclosed herein comprise are use a reporter. A reporter or labeling agent, is a molecule that facilitates the detection of a molecule (e.g., a nucleic acid sequence) to which it is attached. Numerous reporter molecules that may be used to label nucleic acids are known. Direct reporter molecules include fluorophores, chromophores, and radiophores. Non-limiting examples of fluorophores include, a red fluorescent squarine dye such as 2,4-Bis[1,3,3-trimethyl-2-indolinylidenemethyl]cyclobutenediylium-1,3-dio-xolate, an infrared dye such as 2,4 Bis[3,3-dimethyl-2-(1H-benz[e] indolinylidenemethyl)]cyclobutenediylium-1,-3-dioxolate, or an orange fluorescent squarine dye such as 2,4-Bis[3,5-dimethyl-2-pyrrolyl]cyclobutenediylium-1,3-diololate.

Additional non-limiting examples of fluorophores include quantum dots, Alexa Fluor™ dyes, AMCA, BODIPY™ 630/650, BODIPY™ 650/665, BODIPY™-FL, BODIPY™-R6G, BODIPY™-TMR, BODIPY™-TRX, Cascade Blue™, CyDye™, including but not limited to Cy2™, Cy3™, and Cy5™, a DNA intercalating dye, 6-FAM™, Fluorescein, HEX™, 6-JOE, Oregon Green™ 488, Oregon Green™ 500, Oregon Green™ 514, Pacific Blue™, REG, phycobilliproteins including, but not limited to, phycoerythrin and allophycocyanin, Rhodamine Green™, Rhodamine Red™, ROX™, TAMRA™, TET™, Tetramethylrhodamine, or Texas Red™. A signal amplification reagent, such as tyramide (PerkinElmer), may be used to enhance the fluorescence signal. Indirect reporter molecules include biotin, which must be bound to another molecule such as streptavidin-phycoerythrin for detection. Pairs of labels, such as fluorescence resonance energy transfer pairs or dye-quencher pairs, may also be employed.

Labeled amplification products may be labeled directly or indirectly. Direct labeling may be achieved by, for example, using labeled primers, using labeled dNTPs, using labeled nucleic acid intercalating agents, or combinations of the above. Indirect labeling may be achieved by, for example, hybridizing a labeled probe to the amplification product.

The probes and methods disclosed herein may be employed in the detection of target nucleic acid sequences. The target nucleic acid sequence may be any sequence of interest. The sample containing the target nucleic acid sequence may be any sample that contains nucleic acids. In certain aspects of the invention the sample is, for example, a subject who is being screened for the presence or absence of one or more genetic mutations or polymorphisms. In another aspect of the invention the sample may be from a subject who is being tested for the presence or absence of a pathogen. Where the sample is obtained from a subject, it may be obtained by methods known to those in the art such as aspiration, biopsy, swabbing, venipuncture, spinal tap, fecal sample, or urine sample. In some aspects of the invention, the sample is an environmental sample such as a water, soil, or air sample. In other aspects of the invention, the sample is from a plant, bacteria, virus, fungi, protozoan, or metazoan.

Various methods disclosed herein use PCR amplification. Each amplification cycle has three phases: a denaturing phase, a primer annealing phase, and a primer extension phase. The amplification cycle can be repeated until the desired amount of amplification product is produced. Typically, the amplification cycle is repeated between about 10 to 40 times. For real-time PCR, detection of the amplification products will typically be done after each amplification cycle. Although in certain aspects of the invention, detection of the amplification products may be done after every second, third, fourth, or fifth amplification cycle. Detection may also be done such that as few as 2 or more amplification cycles are analyzed or detected. The amplification cycle may be performed in the same chamber in which the detection of the amplification occurs, in which case this chamber would need to comprise a heating element so the temperature in the chamber can be adjusted for the denaturing phase, primer annealing phase, and a primer extension phase of the amplification cycle. The heating element would typically be under the control of a processor. The amplification cycle may, however, be performed in a different chamber from the chamber in which detection of the amplification occurs, in which case the "amplification" chamber would need to comprise a heating element but the "detection" or "imaging" chamber would not be required to have a heating element. Where amplification and detection occur in separate chambers, the fluid in which the amplification reaction occurs may be transferred between the chambers by, for example, a pump or piston. The pump or piston may be under the control of a processor. Alternatively, the fluid may be transferred between the chambers manually using, for example, a pipette.

Certain aspects of the embodiments concern endoribonuclease enzymes and use of such enzymes to specifically cleave probes having a ribonucleotide (RNA) position when the probe is hybridized to a DNA target sequence. In some aspects, the endoribonuclease is an RNAse H, such as RNase HII. In certain specific aspects, the endoribonuclease is a thermostable enzyme or a thermophilic, hotstart enzyme (e.g., a thermostable RNase HII enzyme and a thermophilic, hotstart RNaseHII enzyme).

As mentioned above, the methods disclosed herein may be performed on a sample that is partitioned into a plurality of compartments. Thus, in certain embodiments the methods disclosed herein are compartmentalized in droplets or wells to perform digital PCR reactions. As described in B. Vogelstein, K. W. Kinzler, P.C.R. Digital, Proc Natl Acad Sci USA, 96 (1999), pp. 9236-9241, digital PCR methods may be helpful for distributing the target nucleic acid such that at least some of the reactions contain no target nucleic acid molecules. At certain dilutions the number of amplification positive reactions is equal to the number of template molecules originally present.

As used herein the specification, "a" or "an" may mean one or more. As used herein in the claim(s), when used in conjunction with the word "comprising", the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 7A-7D—A non-limiting exemplary schematic showing a probe of the embodiments.

DESCRIPTION OF ILLUSTRATIVE EMBODIMENTS

I. Exemplary Probe Configurations

By using cleavable probes with unique melt profiles, multiplexing can be achieved in a single-color channel, thus allowing even more multiplexing with multiple color channels. Disclosed are methods and compositions for detecting nucleic acids in a sample. Typically, the methods include detecting signals, such as a signal emitted from a fluorophore. Also disclosed are oligonucleotides, especially probes, which may be used for the detection of target nucleic acids. In particular methods of the embodiments employ cleavable and extendable probes to facilitate multiplexing by generation of multiple melt curves or descrete melt analysis. Varying the length and/or G/C content of the extendable segment (e.g., the melt-signature region or stem region) of the probe gives rise to double-stranded structure with different melt properties allowing for generation of multiple melt-distinguishable probes per reporter.

Figure 1A:
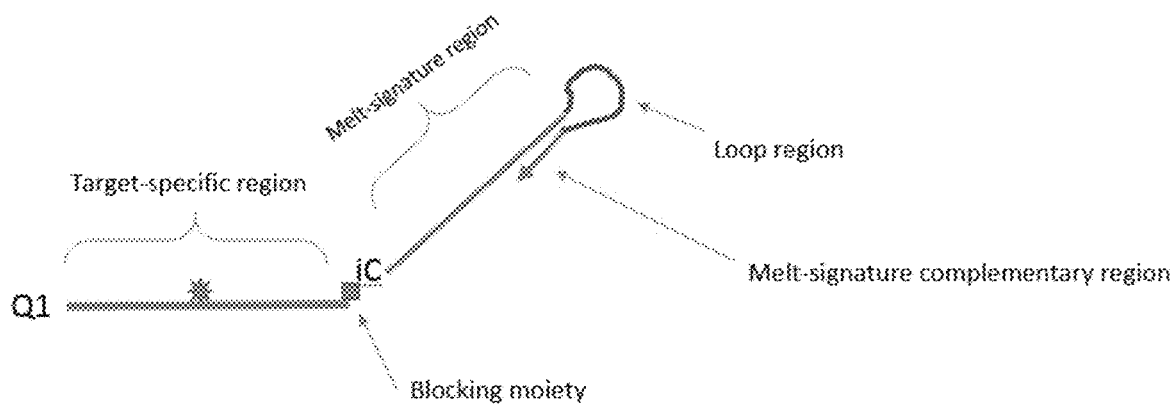
FIG. 1A-C—A non-limiting exemplary schematic showing a probe of the embodiments.
Figure 1B:
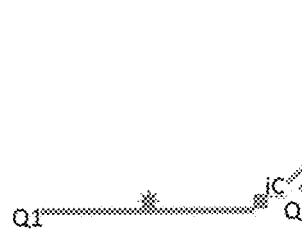
Figure 1C:
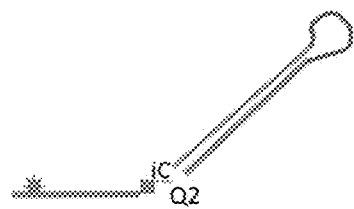

FIGS. 1A-1C show a schematic of a probe of according to one embodiment of the invention. As shown in FIG. 1A, the probe comprises a target-specific region bounded by a quencher (indicated by Q1) at its 5' end and a polymerase blocking moiety at its 3' end (indicated by the square symbol). The target-specific region also includes a reporter (indicated by the star symbol). The quencher and reporter are located such that when the 5' to 3' exonuclease activity of a polymerase acts on the probe, the quencher will be cleaved from the probe but the reporter will not be cleaved. The probe also includes a melt-signature region and a melt-signature complementary region, which are configured to hybridize with each other to form a hairpin structure as shown in FIG. 1A. The loop region facilitates the formation of the loop in the hairpin structure. The melt-signature complementary region has a free 3' —OH group and, thus, can function as a primer for a DNA polymerase. The melt-signature region includes a non-naturally occurring nucleotide, which in this case is an isoC. When the melt-signature complementary region is extended by a DNA polymerase in the presence of a complementary non-naturally occurring nucleotide, such as an isoG in this embodiment, the complementary non-naturally occurring nucleotide is incorporated into the synthesized sequence as shown in FIGS. 1B and 1C.

As shown in FIGS. 1B and 1C, the melt-signature complementary region has been extended and a quencher-labelled isodGTP (indicated by Q2) has been incorporated opposite the isoC of the melt-signature region. In FIG. 1C, the target-specific region has been partially cleaved resulting in a truncated probe that retains the reporter but not the quencher Q1. In its hybridized hairpin form, quencher Q2 remains in proximity to the reporter such that it is able to exert a quenching effect on the reporter. However, when the probe is melted the distance between the reporter and Q2 is increased resulting in a greater detectable signal from the reporter. In FIG. 1B, the target-specific region has not been cleaved. Accordingly, the reporter is subject to quenching effects from both Q1 and Q2. When the probe depicted in FIG. 1B is melted, the distance between the reporter and Q2 is increased but due to the presence of Q1 any increase in detectable signal from the reporter is measurably less than with the probe depicted in FIG. 1C where Q1 is absent.

Figure 2:
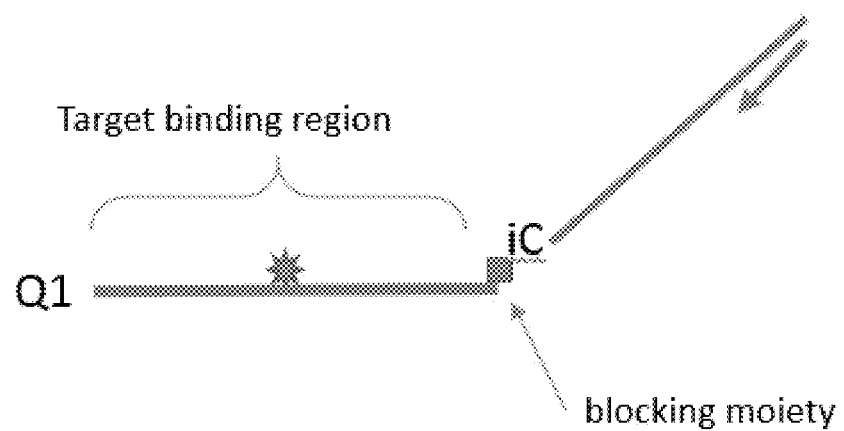
FIG. 2—A non-limiting exemplary probe construct of the embodiments.

The probe embodiments shown in FIG. 1A-1C comprise hairpin structures. An alternative probe configuration that employs two probe molecules rather than unimolecular hairpin probe is shown in FIG. 2.

Figure 3A:
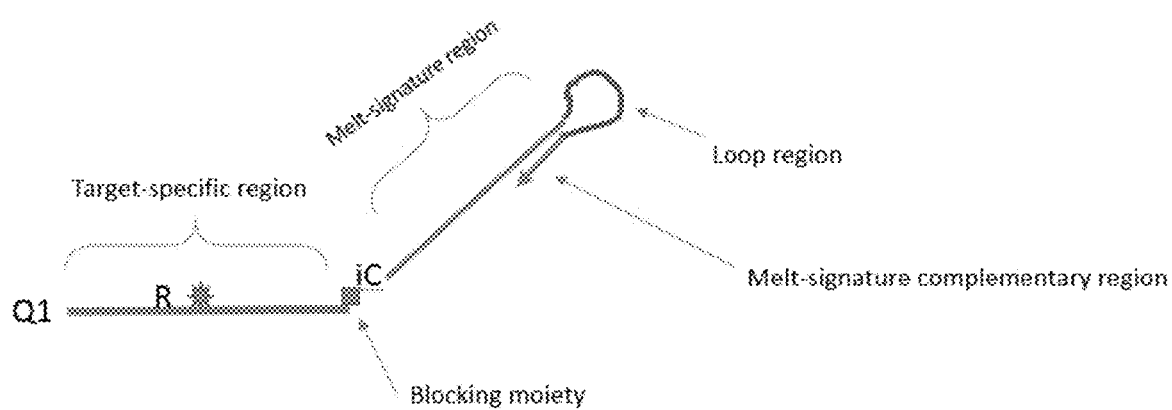
FIG. 3A-3C—A non-limiting exemplary schematic showing a probe of the embodiments.
Figure 3B:
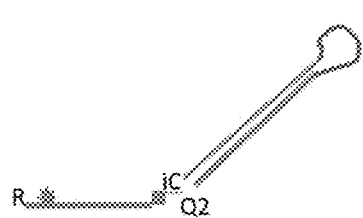
Figure 3C:
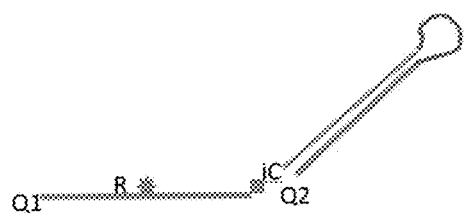

FIGS. 3A-3C show a schematic of a probe of according to another embodiment of the invention. As shown in FIG. 3A, the probe comprises a target-specific region bounded by a quencher (indicated by Q1) at its 5' end and a polymerase blocking moiety at its 3' end (indicated by the square symbol). The target-specific region also includes a reporter (indicated by the star symbol) and a ribobase (indicated by the R). The ribobase is located between the quencher and reporter such that when an enzyme having endoribonuclease activity acts on the probe, the quencher will be cleaved from the probe but the reporter remains attached to the probe. The probe also includes a melt-signature region and a melt-signature complementary region, which are configured to hybridize with each other to form a hairpin structure as shown in FIG. 3A. The loop region facilitates the formation of the loop in the hairpin structure. The melt-signature complementary region has a free 3' —OH group and, thus, can function as a primer for a DNA polymerase. The melt-signature region includes a non-naturally occurring nucleotide, which in this case is an isoC. When the melt-signature complementary region is extended by a DNA polymerase in the presence of a complementary non-naturally occurring nucleotide, such as an isoG in this embodiment, the complementary non-naturally occurring nucleotide is incorporated into the synthesized sequence as shown in FIGS. 3B and 3C.

As shown in FIGS. 3B and 3C, the melt-signature complementary region has been extended and a quencher-labelled isodGTP (indicated by Q2) has been incorporated opposite the isoC of the melt-signature region. In FIG. 3B, the target-specific region has been cleaved resulting in a truncated probe that retains the reporter but not the quencher Q1. In its hybridized hairpin form, quencher Q2 remains in proximity to the reporter such that it is able exert a quenching effect on the reporter. However, when the probe is melted the distance between the reporter and Q2 is increased resulting in a greater detectable signal from the reporter. In FIG. 3C, the target-specific region has not been cleaved due to a failure to hybridize to a complementary target sequence. Accordingly, the reporter is subject to quenching effects from both Q1 and Q2. When the probe depicted in FIG. 3C is melted, the distance between the reporter and Q2 is increased but due to the presence of Q1 any increase in detectable signal from the reporter is measurably less than with the probe depicted in FIG. 3B where Q1 is absent.

The melt-signature region of any of the probes shown in FIGS. 1A-1C, FIG. 2, or FIGS. 3A-3C can be configured to have a desired melting temperature by, for example, adjusting the melt-signature region's length and/or GC-content. In this way, multiple different probes can be designed to have double-stranded regions with different melt temperatures. Accordingly, these probes can be distinguished from one another by melt analysis even if the probes are labelled with the same or indistinguishable reporters (e.g., labelled with the same fluorescent dye).

Figure 4:
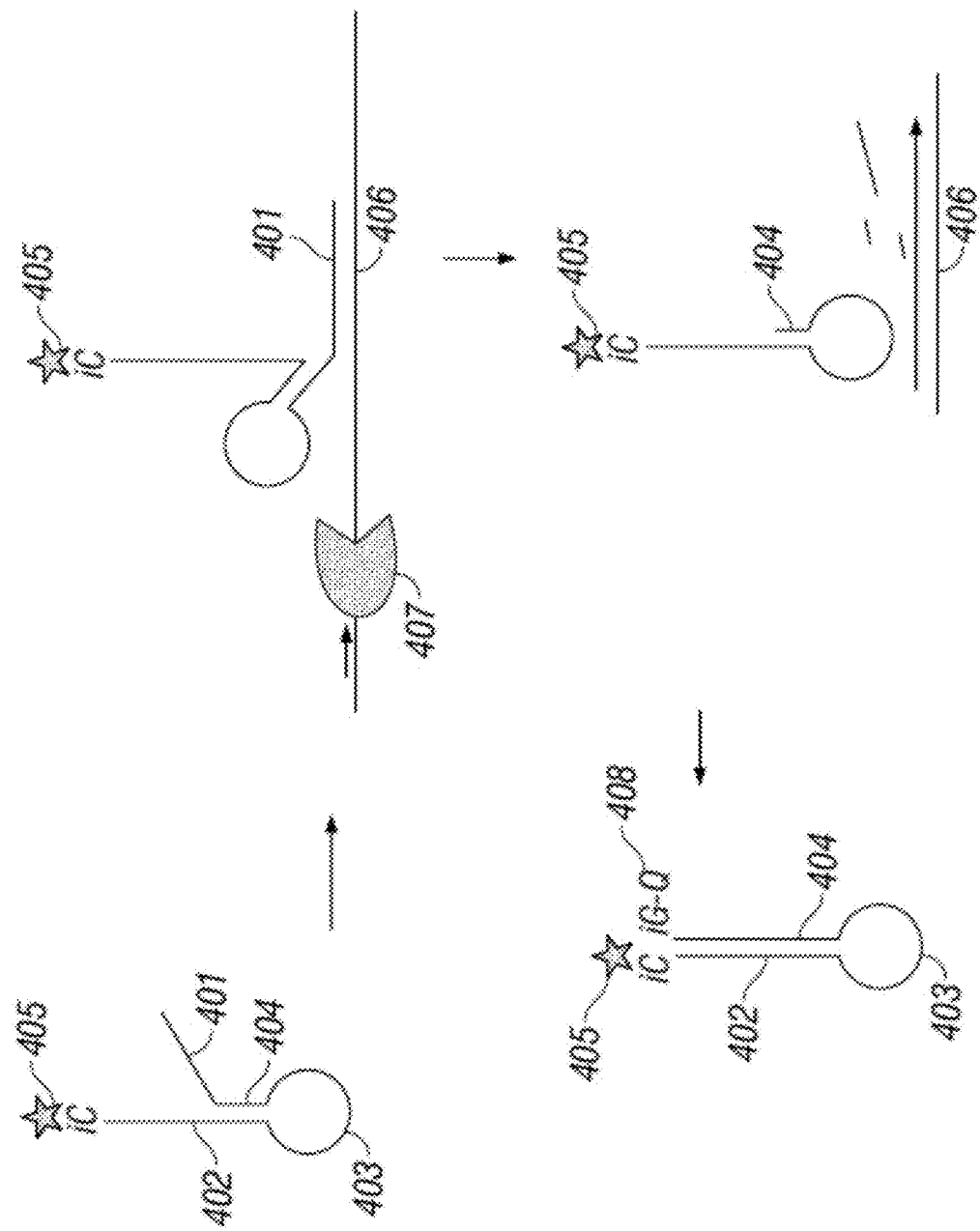
FIG. 4—A non-limiting exemplary schematic showing a probe of the embodiments.

FIG. 4 shows a schematic of a probe of according to yet another embodiment of the invention. The probe comprises a target-specific region (401), a first stem-forming region (402), a loop region (403), a second stem forming region (404), which is the reverse complement of a portion of the first stem-forming region (402), and a labelled region (405). Labelled region (405) in FIG. 4 comprises a reporter labelled iso C. In use, target-specific region (401) hybridizes to a complementary sequence of a target (406). As DNA polymerase (407) extends along target (406), the target-specific region (401) is cleaved from the probe. Second stem forming region (404) hybridizes to first stem-forming region (402). Second stem forming region (404) has a free 3' —OH that is then extended along first stem-forming region (402) by a DNA polymerase. The DNA polymerase incorporated a quencher labelled isoG opposite the reporter labelled isoC of the labelled region (405). In its hybridized hairpin form the signal from the reporter is quenched by the quencher. However, when the probe is melted the distance between the reporter and quencher is increased resulting in a greater detectable signal from the reporter.

FIGS. 7A-7D show a schematic of a probe of according to yet another embodiment of the invention. In FIG. 7A, a probe for detecting the presence of a target nucleic acid is provided, the probe comprising, from 5' to 3': (a) a melt signature region comprising a first nucleotide sequence that is not complimentary to the target nucleotide sequence and includes at least one non-naturally occurring nucleotide and a region that is complimentary to an extensible oligonucleotide sequence that is 3' to the non-naturally occurring nucleotide; (b) a target-specific region comprising a first nucleotide sequence complementary to a target nucleotide sequence, a reporter, a ribobase, and a quencher, wherein the reporter is coupled to the target-specific region at a first location that is 5' relative to the ribobase and the quencher, and the quencher is coupled to the target-specific region at a second location that is 3' relative to the reporter and the ribobase, In FIG. 7B the melt-signature complementary region has been extended by a separate extensible oligonucleotide sequence and a quencher-labelled isodGTP (indicated by iG-Q2) has been incorporated opposite the isoC of the melt-signature region. In FIG. 7C, the target-specific region has been cleaved by an endoribonuclease resulting in a truncated probe that retains the reporter but not the quencher Q1. In its hybridized form, quencher iG-Q2 remains in proximity to the reporter such that it is able exert a quenching effect on the reporter. However, when the probe is melted in FIG. 7D the distance between the reporter and Q2 is increased resulting in a greater detectable signal from the reporter.

Figure 5:
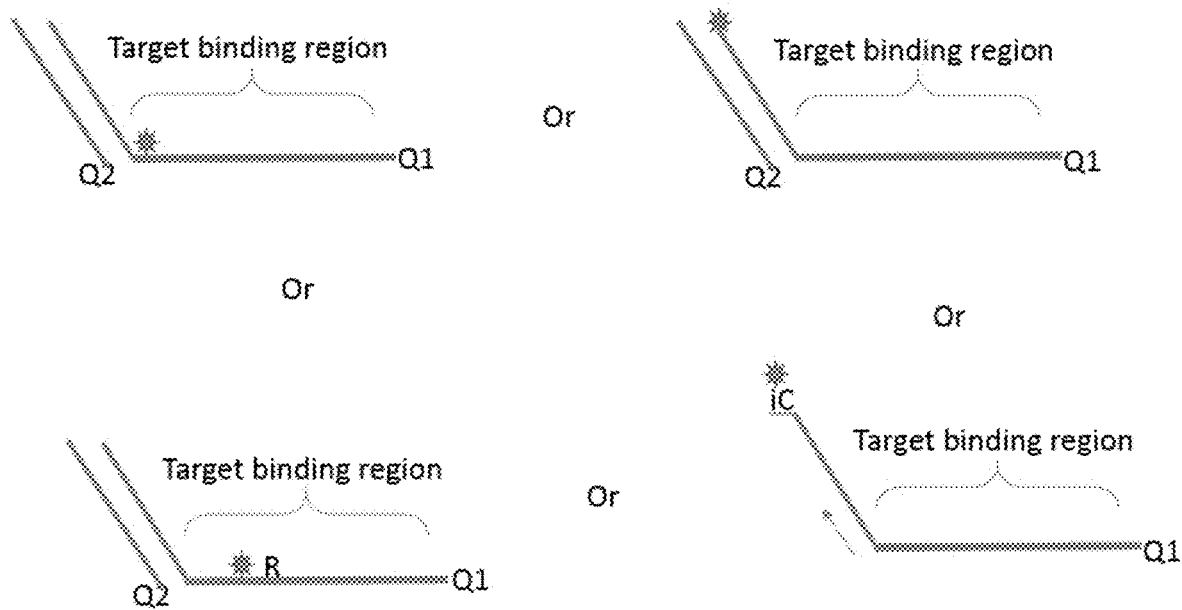
FIG. 5—Non-limiting exemplary probe constructs of the embodiments
Figure 6:
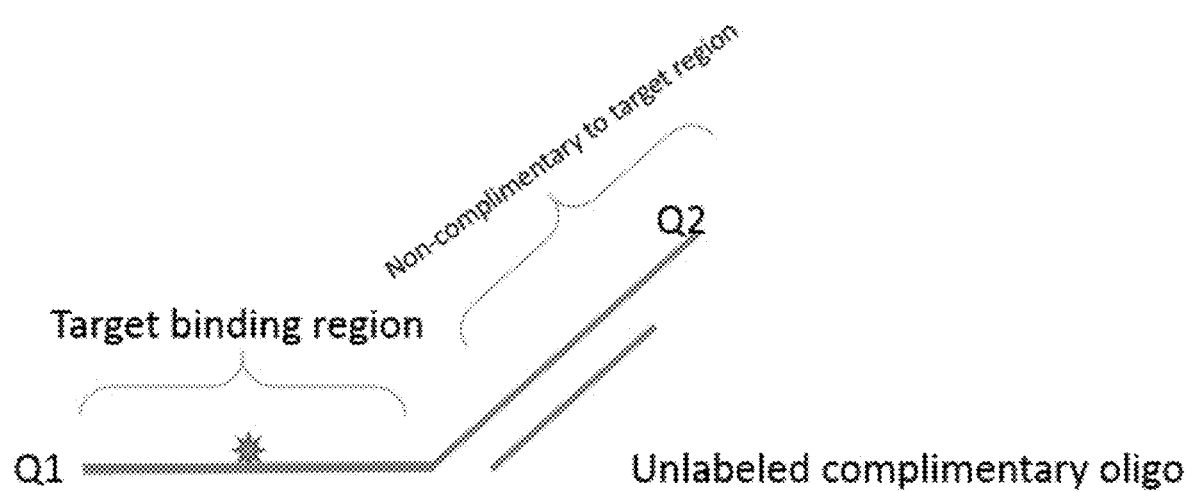
FIG. 6—A non-limiting exemplary probe construct of the embodiments.

Additional embodiments of cleavable probes that may be used in the methods disclosed herein are shown in FIG. 5 and FIG. 6.

II. Nucleic Acids

As used herein "nucleic acid" means either DNA or RNA, single-stranded or double-stranded, and any chemical modifications thereof. Modifications include, but are not limited to, those which provide other chemical groups that incorporate additional charge, polarizability, hydrogen bonding, electrostatic interaction, and fluxionality to the nucleic acid ligand bases or to the nucleic acid ligand as a whole. Such modifications include, but are not limited to, 2'-position sugar modifications, 5-position pyrimidine modifications, 8-position purine modifications, modifications at exocyclic amines, substitution of 4-thiouridine, substitution of 5-bromo or 5-iodo-uracil, backbone modifications, methylations, and unusual base-pairing combinations, such as the isobases. Accordingly, the nucleic acids described herein include not only the standard bases adenine (A), cytosine (C), guanine (G), thymine (T), and uracil (U) but also non-standard or non-natural nucleotides. Non-standard or non-natural nucleotides, which form hydrogen-bonding base pairs, are described, for example, in U.S. Pat. Nos. 5,432,272, 5,965,364, 6,001,983, 6,037,120, and 6,140,496, all of which are incorporated herein by reference. By "non-standard nucleotide" or "non-natural nucleotide" it is meant a base other than A, G, C, T, or U that is susceptible to incorporation into an oligonucleotide and that is capable of base-pairing by hydrogen bonding, or by hydrophobic, entropic, or van der Waals interactions, with a complementary non-standard or non-natural nucleotide to form a base pair. Some examples include the base pair combinations of iso-C/iso-G, K/X, K/P, H/J, and M/N, as illustrated in U.S. Pat. No. 6,037,120, incorporated herein by reference.

The hydrogen bonding of these non-standard or non-natural nucleotide pairs is similar to those of the natural bases where two or three hydrogen bonds are formed between hydrogen bond acceptors and hydrogen bond donors of the pairing non-standard or non-natural nucleotides. One of the differences between the natural bases and these non-standard or non-natural nucleotides is the number and position of hydrogen bond acceptors and hydrogen bond donors. For example, cytosine can be considered a donor/acceptor/acceptor base with guanine being the complementary acceptor/donor/donor base. Iso-C is an acceptor/acceptor/donor base and iso-G is the complementary donor/donor/acceptor base, as illustrated in U.S. Pat. No. 6,037,120, incorporated herein by reference.

Other non-natural nucleotides for use in oligonucleotides include, for example, naphthalene, phenanthrene, and pyrene derivatives as discussed, for example, in Ren, et al., J. Am. Chem. Soc. 1996, 118:1671 and McMinn et al., J. Am. Chem. Soc. 1999, 121:11585, both of which are incorporated herein by reference. These bases do not utilize hydrogen bonding for stabilization, but instead rely on hydrophobic or van der Waals interactions to form base pairs.

As used herein, an oligonucleotide is understood to be a molecule that has a sequence of bases on a backbone comprised mainly of identical monomer units at defined intervals. The bases are arranged on the backbone in such a way that they can enter into a bond with a nucleic acid having a sequence of bases that are complementary to the bases of the oligonucleotide. The most common oligonucleotides have a backbone of sugar phosphate units. A distinction may be made between oligodeoxyribonucleotides, made up of "dNTPs," which do not have a hydroxyl group at the 2' position, and oligoribonucleotides, made up of "NTPs," which have a hydroxyl group in the 2' position. Oligonucleotides also may include derivatives, in which the hydrogen of the hydroxyl group is replaced with an organic group, e.g., an allyl group.

An oligonucleotide is a nucleic acid that includes at least two nucleotides. An oligonucleotide may be designed to function as a "primer." A "primer" is a short nucleic acid, usually a ssDNA oligonucleotide, which may be annealed to a target polynucleotide by complementary base-pairing. The primer may then be extended along the target DNA or RNA strand by a polymerase enzyme, such as a DNA polymerase enzyme. Primer pairs can be used for amplification (and identification) of a nucleic acid sequence (e.g., by the polymerase chain reaction (PCR)). An oligonucleotide may be designed to function as a "probe." A "probe" refers to an oligonucleotide, its complements, or fragments thereof, which are used to detect identical, allelic, or related nucleic acid sequences. Probes may include oligonucleotides that have been attached to a detectable label or reporter molecule. Typical labels include fluorescent dyes, quenchers, radioactive isotopes, ligands, scintillation agents, chemiluminescent agents, and enzymes.

An oligonucleotide may be designed to be specific for a target nucleic acid sequence in a sample. For example, an oligonucleotide may be designed to include "antisense" nucleic acid sequence of the target nucleic acid. As used herein, the term "antisense" refers to any composition capable of base-pairing with the "sense" (coding) strand of a specific target nucleic acid sequence. An antisense nucleic acid sequence may be "complementary" to a target nucleic acid sequence. As used herein, "complementarity" describes the relationship between two single-stranded nucleic acid sequences that anneal by base-pairing. For example, 5'-AGT-3' pairs with its complement, 3'-TCA-5'. In some embodiments, primers or probes may be designed to include mismatches at various positions. As used herein, a "mismatch" means a nucleotide pair that does not include the standard Watson-Crick base pairs, or nucleotide pairs that do not preferentially form hydrogen bonds. The mismatch may include a natural nucleotide or a non-natural or non-standard nucleotide substituted across from a particular base or bases in a target. For example, the probe or primer sequence 5'-AGT-3' has a single mismatch with the target sequence 3'-ACA-5'. The 5' "A" of the probe or primer is mismatched with the 3' "A" of the target. Similarly, the target sequence 5'-AGA-3' has a single mismatch with the probe or primer sequence 3'-(iC)CT-5'. Here an iso-C is substituted in place of the natural "T." However, the sequence 3'-(iC)CT-5' is not mismatched with the sequence 5'-(iG)GA-3'.

Oligonucleotides may also be designed as degenerate oligonucleotides. As used herein, "degenerate oligonucleotide" is meant to include a population, pool, or plurality of oligonucleotides comprising a mixture of different sequences where the sequence differences occur at a specified position in each oligonucleotide of the population. Various substitutions may include any natural or non-natural nucleotide, and may include any number of different possible nucleotides at any given position. For example, the above degenerate oligonucleotide may instead include R=iC or iG, or R=A or G or T or C or iC or iG.

Oligonucleotides, as described herein, typically are capable of forming hydrogen bonds with oligonucleotides having a complementary base sequence. These bases may include the natural bases, such as A, G, C, T, and U, as well as artificial, non-standard or non-natural nucleotides such as iso-cytosine and iso-guanine. As described herein, a first sequence of an oligonucleotide is described as being 100% complementary with a second sequence of an oligonucleotide when the consecutive bases of the first sequence (read 5'-to-3') follow the Watson-Crick rule of base pairing as compared to the consecutive bases of the second sequence (read 3'-to-5'). An oligonucleotide may include nucleotide substitutions. For example, an artificial base may be used in place of a natural base such that the artificial base exhibits a specific interaction that is similar to the natural base.

An oligonucleotide that is specific for a target nucleic acid also may be specific for a nucleic acid sequence that has "homology" to the target nucleic acid sequence. As used herein, "homology" refers to sequence similarity or, interchangeably, sequence identity, between two or more polynucleotide sequences or two or more polypeptide sequences. The terms "percent identity" and "% identity" as applied to polynucleotide sequences, refer to the percentage of residue matches between at least two polynucleotide sequences aligned using a standardized algorithm (e.g., BLAST).

An oligonucleotide that is specific for a target nucleic acid will "hybridize" to the target nucleic acid under suitable conditions. As used herein, "hybridization" or "hybridizing" refers to the process by which an oligonucleotide single strand anneals with a complementary strand through base pairing under defined hybridization conditions. "Specific hybridization" is an indication that two nucleic acid sequences share a high degree of complementarity. Specific hybridization complexes form under permissive annealing conditions and remain hybridized after any subsequent washing steps. Permissive conditions for annealing of nucleic acid sequences are routinely determinable by one of ordinary skill in the art and may occur, for example, at 65° C. in the presence of about 6×SSC. Stringency of hybridization may be expressed, in part, with reference to the temperature under which the wash steps are carried out. Such temperatures are typically selected to be about 5° C. to 20° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. Equations for calculating $T_m$, for example, nearest-neighbor parameters, and conditions for nucleic acid hybridization are known in the art.

As used herein, "amplification" or "amplifying" refers to the production of additional copies of a nucleic acid sequence. Amplification is generally carried out using polymerase chain reaction (PCR) technologies known in the art. The term "amplification reaction system" refers to any in vitro means for multiplying the copies of a target sequence of nucleic acid. The term "amplification reaction mixture" refers to an aqueous solution comprising the various reagents used to amplify a target nucleic acid. These may include enzymes (e.g., a thermostable polymerase), aqueous buffers, salts, amplification primers, target nucleic acid, nucleoside triphosphates, and optionally, at least one labeled probe and/or optionally, at least one agent for determining the melting temperature of an amplified target nucleic acid (e.g., a fluorescent intercalating agent that exhibits a change in fluorescence in the presence of double-stranded nucleic acid).

The amplification methods described herein may include "real-time monitoring" or "continuous monitoring." These terms refer to monitoring multiple times during a cycle of PCR, preferably during temperature transitions, and more preferably obtaining at least one data point in each temperature transition. The term "homogeneous detection assay" is used to describe an assay that includes coupled amplification and detection, which may include "real-time monitoring" or "continuous monitoring."

Amplification mixtures may include natural nucleotides (including A, C, G, T, and U) and non-natural or non-standard nucleotides (e.g., including iC and iG). DNA and RNA oligonucleotides include deoxyriboses or riboses, respectively, coupled by phosphodiester bonds. Each deoxyribose or ribose includes a base coupled to a sugar. The bases incorporated in naturally-occurring DNA and RNA are adenosine (A), guanosine (G), thymidine (T), cytosine (C), and uridine (U). These five bases are "natural bases." According to the rules of base pairing elaborated by Watson and Crick, the natural bases hybridize to form purine-pyrimidine base pairs, where G pairs with C and A pairs with T or U. These pairing rules facilitate specific hybridization of an oligonucleotide with a complementary oligonucleotide.

The oligonucleotides and nucleotides of the disclosed methods may be labeled with a quencher. Quenching may include dynamic quenching (e.g., by FRET), static quenching, or both. Suitable quenchers may include Dabcyl. Suitable quenchers may also include dark quenchers, which may include black hole quenchers sold under the trade name "BHQ" (e.g., BHQ-0, BHQ-1, BHQ-2, and BHQ-3, Biosearch Technologies, Novato, CA). Dark quenchers also may include quenchers sold under the trade name "QXL™" (Anaspec, San Jose, CA). Dark quenchers also may include DNP-type non-fluorophores that include a 2,4-dinitrophenyl group.

III. Compartmentalized Reactions

The methods and compositions disclosed herein may be used in compartmentalized reactions. One approach for compartmentalizing reactions is by using droplets, which are isolated volumes of a first fluid that are completely surrounded by a second fluid or by a second fluid and one or more surfaces. Another approach for compartmentalizing reactions is by using a plurality of wells or chambers formed in a substrate. The droplets or chambers may be imaged by a variety of techniques. For example, detection may comprise imaging fluorescent wavelengths and/or fluorescent intensities emitted from the labeled hairpin probes in each compartment. Non-limiting examples of imaging systems that could be adapted for use with the methods and compositions disclosed herein are described in U.S. Pat. No. 8,296,088 and U.S. Pat. Publ. 2012/0288897, which are incorporated herein by reference.

As discussed above, the polymerase chain reaction (PCR) is an example of a reaction that may be performed within a droplet or other compartment. In particular, droplets are useful in digital PCR (dPCR) techniques. dPCR involves partitioning the sample such that individual nucleic acid molecules contained in the sample are localized in many separate regions, such as in individual wells in microwell plates, in the dispersed phase of an emulsion, or arrays of nucleic acid binding surfaces. Each partition (e.g., droplet) will contain 0 or greater than zero molecules, providing a negative or positive reaction, respectively. Unlike conventional PCR, dPCR is not dependent on the number of amplification cycles to determine the initial amount of the target nucleic acid in the sample. Accordingly, dPCR eliminates the reliance on exponential data to quantify target nucleic acids and provides absolute quantification. Bead emulsion PCR, which clonally amplifies nucleic acids on beads in an emulsion, is one example of a dPCR technique in which the reactions are portioned into droplets. See, e.g., U.S. Pat. Nos. 8,048,627 and 7,842,457, which are hereby incorporated by reference.

II. Melt Analysis

Various probes disclosed herein are designed with labels and melt properties to uniquely identify the target sequences that the probes are designed to hybridize to. Methods employing such probes may use various melt analyses, such as those described below, to identify the probes and thereby the presence or absence of the target nucleic acid sequences the probes were designed to detect.

A melting curve (dissociation curve) charts the change in fluorescence observed when double-stranded DNA dissociates or "melts" into single-stranded DNA as the temperature of the reaction is raised. For example, when double-stranded DNA is slowly heated in the presence of intercalating dyes, a sudden decrease in fluorescence is detected as the melting point (Tm) is reached and the dye dissociates from the duplex. Because the Tm of nucleic acids is affected by length, GC content, and the presence of base mismatches, among other factors, different duplex nucleic acids can be distinguished by their different melting characteristics.

High-resolution melt curve (HRM) analysis is a homogeneous, post-amplification method for identifying single nucleotide differences, e.g., SNPs, novel mutations, and methylation patterns. HRM analysis is a more sensitive approach to traditional melt curve profiling, in which double-stranded DNA is monitored for the temperature (Tm) at which it dissociates into single-stranded DNA. In HRM, the amplification reaction is subjected to smaller, incremental temperature increases (typically 0.1-1° C. per minute) while fluorescence is monitored continuously. In the presence of intercalating dyes that bind double-strand nucleic acids, fluorescence decreases slowly until the temperature approaches the product Tm and at the Tm, a dramatic decrease in fluorescence is observed as the sample transitions from double stranded to single stranded DNA. Since Tm is dependent on, amongst other things, nucleotide sequence and the presence of mismatched nucleotides in a duplex, mutations can be detected in HRM analysis as either a shift in Tm or as a change in shape of the melting curve. In contrast to traditional melt curve analysis, HRM can provide single-nucleotide discrimination between amplicons. By taking fluorescence measurements at many temperature intervals—at 2° C. intervals or smaller, such as at 1° C., 0.5° C., 0.3° C., 0.2° C., or even 0.1° C. intervals—one can track the rate of change of fluorescence intensity (i.e., the derivative of the fluorescence intensity with respect to temperature) and determine the temperature or temperatures (Tm) at which significant melt activity occurred.

Traditionally, in dPCR applications, post-amplification end-point measurements of fluorescence in individual partitions have been used to determine the presence or absence of a target nucleic acid in a sample. More recently, melt analysis using intercalating dyes has been used to specifically identify target nucleic acids in dPCR. To distinguish between mere noise and an actual presence of a melt event, a threshold is set for either or both the RFU plots and negative-derivative plots. For an RFU plot, a signal threshold could be selected by using a percentage of the standard deviation of a slope-corrected control curve, e.g., 200%, 300%, 400%, 500%, 1000%, or 2000% of the standard deviation. Then, if the fluorescence intensity changes beyond the threshold amount across a given melt temperature window (e.g., 60 to 70° C. for a target probe whose melt temperature is expected to be 65° C.), the target is deemed to be present. For a negative-derivative plot, a signal threshold is selected by using a percentage of the standard deviation of the negative derivative of the slope-corrected RFU curve for a control sample, e.g., 200%, 300%, 400%, 500%, 1000%, or 2000% of the standard deviation. Then, if the any negative-derivative low peaks are more than the threshold magnitude below zero, a positive melt event occurred for the relevant target probe, and the corresponding target was present in that compartment. Threshold values can alternatively be set by considering historical data and using a fraction of typical magnitudes of the negative-derivative melt peaks. For example, a threshold might be set anywhere from 10% to 50% of the average negative-derivative melt peak magnitude for that specific target probe.

US2016/0310949, which is incorporated herein by reference, describes using unique melt signatures generated from traditional or high resolution melt analysis (HRM) in a digital microfluidic system to achieve quantitative multiplexing in dPCR. WO2015023616, which is incorporated herein by reference, describes a digital system in which target nucleic acids are non-specifically amplified using universal primers and HRM analysis is used to identify individual bacterial species. Melt signatures in individual wells containing target nucleic acids are compared to standard melt curves to identify the target sequence present. Accurate identification of individual bacterial species requires careful comparison of melt profiles among unique targets, and therefore relies on high resolution melt data, typically $\Delta T < 1°$ C.

Discrete Melt Analysis (DMA) provides a method for performing melt analysis that requires fewer measurements of fluorescence versus temperature and thus results in faster data collection and analysis, and consequently provides lower turnaround times for assays. As a concept, DMA represents an under-sampling of continuous melt or HRM analysis. In contrast to the latter two methods, DMA requires measurement of fluorescence at only 2 temperatures per target and does not require the calculation of a Tm to identify a target nucleic acid. Fluorescence images are acquired at (1) a temperature at which all probes or duplex nucleic acids representing a particular target are in a hybridized, duplex conformation and (2) a temperature at which all probes or duplex nucleic acids representing the target are fully denatured. Use of appropriate labeling schemes that distinguish these 2 conformations permits detection of changes of conformation at the two measurement temperatures in the presence of target. DMA is particularly well suited to melt analysis performed using probes such as those described herein, and provides an efficient and cost-effective means of multiplexing in digital amplification systems. Use of probes having pre-determined Tms in DMA permits measuring fluorescence at temperature intervals between pre-determined melt peaks to elucidate target presence.

REFERENCES

The following references, to the extent that they provide exemplary procedural or other details supplementary to those set forth herein, are specifically incorporated herein by reference.

U.S. Pat. Nos. 4,942,124; 4,284,412; 4,989,977; 4,498,766; 5,478,722; 4,857,451; 4,774,189; 4,767,206; 4,714,682; 5,160,974; 4,661,913; 5,654,413; 5,656,493; 5,716,784; 5,736,330; 5,837,832; 5,837,860; 5,981,180; 5,994,056; 5,736,330; 5,981,180; 6,057,107; 6,030,787; 6,046,807; 6,057,107; 6,103,463; 6,139,800; 6,174,670; 6,268,222; 6,322,971; 6,366,354; 6,410,278; 6,411,904; 6,449,562; 6,514,295; 6,524,793; 6,528,165; 6,592,822; 6,939,720; 6,977,161; 7,226,737; 7,645,868; 7,955,802; 9,657,332; and 9,982,291

U.S. Published Publication Nos. 2005/0191625; 2008/0182312; 2009/0148849; 2018/0073056; 2018/0073064

PCT Publication No. WO/2016/101959

What is claimed is:

1. A method for detecting the presence of a target nucleic acid comprising:
   (a) contacting a sample with a first primer comprising a first nucleotide sequence complementary to a first portion of the target nucleotide sequence and a probe, the probe comprising, from 5' to 3', (i) a target-specific region comprising a second nucleotide sequence, wherein the second nucleotide sequence is complementary to a second portion of the target nucleotide sequence, wherein the second portion of the target nucleotide sequence is located downstream of the first portion, wherein the second nucleotide sequence is labelled with a first quencher and a fluorophore, and wherein the first quencher is located 5' relative to the fluorophore; (ii) a polymerase extension-blocking moiety; (iii) a melt-signature region comprising a third nucleotide sequence, wherein the third nucleotide sequence is not complementary to the target nucleotide sequence, and wherein the third nucleotide sequence includes a first non-naturally occurring nucleotide, wherein the first non-naturally occurring nucleotide is an isoC nucleotide or an isoG nucleotide; (iii) a loop region; and (iv) a melt-signature complementary region comprising a fourth nucleotide sequence, wherein the forth nucleotide sequence is complementary to a portion of the third nucleotide sequence;
   (b) hybridizing the melt-signature region with the melt-signature complementary region to form a first hairpin structure having a first melting temperature;
   (c) extending the melt-signature complementary region along the melt-signature region using a polymerase to form a second hairpin structure having a second melting temperature, wherein during the extending the polymerase incorporates a second non-naturally occurring nucleotide into the second hairpin structure that is complementary to the first non-naturally occurring nucleotide, wherein the second non-naturally occurring nucleotide is labelled with a second quencher, and wherein the second melting temperature is higher than the first melting temperature;
   (d) hybridizing the first primer to the first portion of the target nucleotide sequence and hybridizing the probe to the second portion of the target nucleotide sequence if the target nucleotide is present in the sample;
   (e) extending the first primer along the target nucleotide sequence using a polymerase having 5' nuclease activity to partially cleave the target-specific region of the probe, wherein the partial cleaving cleaves a portion of the probe labelled with the first quencher and does not cleave a portion of the probe labelled with the fluorophore;
   (f) taking a measurement of a fluorescent signal at at least a first temperature that is below the second melting temperature and a measurement of a fluorescent signal at at least a second temperature that is above the second melting temperature; and
   (d) detecting the presence of the target nucleic acid if there is a change in the fluorescence signal measured below the second melting temperature as compared to the fluorescence signal measured above the second melting temperature indicative of the absence of the first quencher from the second hairpin structure as a result of the partial cleavage of the target-specific region of the probe.

2. A method for detecting the presence of a target nucleic acid comprising:
   (a) contacting a sample with:
      a pair of primers configured to hybridize to opposite strands of the target nucleotide sequence; and
      a probe, the probe comprising, from 5' to 3', (i) a target-specific region comprising a first nucleotide sequence, wherein the first nucleotide sequence is complementary to a portion of the target nucleotide sequence bounded by the primer pair, wherein the first nucleotide sequence is labelled with a first quencher and a fluorophore, and wherein the first quencher is located 5' relative to the fluorophore; (ii) a polymerase extension-blocking moiety; (iii) a melt-signature region comprising a second nucleotide sequence, wherein the second nucleotide sequence is not complementary to the target nucleotide sequence, and wherein the second nucleotide sequence includes a first non-naturally occurring nucleotide, wherein the first non-naturally occurring nucleotide is an isoC nucleotide or an isoG nucleotide; (iii) a loop region; and (iv) a melt-signature complementary region comprising a third nucleotide sequence, wherein the third nucleotide sequence is complementary to a portion of the second nucleotide sequence;
   (b) hybridizing the melt-signature region with the melt-signature complementary region to form a first hairpin structure having a first melting temperature;
   (c) extending the melt-signature complementary region along the melt-signature region using a polymerase to form a second hairpin structure having a second melting temperature, wherein during the extending the polymerase incorporates a second non-naturally occurring nucleotide into the second hairpin structure that is complementary to the first non-naturally occurring nucleotide, wherein the second non-naturally occurring nucleotide is labelled with a second quencher, and wherein the second melting temperature is higher than the first melting temperature;
   (d) hybridizing the primer pair to the opposite strands of the target nucleotide sequence and hybridizing the probe to the first portion of the target nucleotide sequence, if the target nucleotide is present in the sample;
   (e) extending the primer pair along the opposite strands of the target nucleotide sequence using a polymerase having 5' nuclease activity to partially cleave the target-specific region of the probe, wherein the partial cleaving cleaves a portion of the probe labelled with the first quencher and does not cleave a portion of the probe labelled with the fluorophore;
   (f) taking a measurement of a fluorescent signal at at least a first temperature that is below the second melting temperature and a measurement of a fluorescent signal at at least a second temperature that is above the second melting temperature; and
   (g) detecting the presence of the target nucleic acid if there is a change in the fluorescence signal measured below the second melting temperature as compared to the fluorescence signal measured above the second melting temperature indicative of the absence of the first quencher from the second hairpin structure as a result of the partial cleavage of the target-specific region of the probe.

3. The method of claim 2, wherein steps (d) and (e) are performed after steps (b) and (c).

4. The method of claim 2, wherein steps (d) and (e) are performed before steps (b) and (c).

5. The method of claim 2, comprising repeating steps (b) through (f) through multiple PCR cycles.

6. The method of claim 2, comprising repeating steps (d) and (e) through multiple PCR cycles prior to performing steps (b), (c), (f), and (g).

7. The method of claim 2, further comprising partitioning the sample into a plurality of partitions such that, if the target nucleic acid is present in the sample, at least one partition of the plurality of partitions will not contain a target nucleic acid, wherein the partitioning of the sample is performed prior to performing at least step (e).

8. The method of claim 7, wherein the partitioning of the sample is performed prior to performing any of steps (b) through (g).

9. A method for detecting the presence of two or more target nucleic acids comprising:
(a) contacting a sample with:
a first pair of primers configured to hybridize to opposite strands of a first target nucleotide sequence;
a second pair of primers configured to hybridize to opposite strands of a second target nucleotide sequence;
a first probe, the first probe comprising, from 5' to 3', (i) a target-specific region comprising a first nucleotide sequence, wherein the first nucleotide sequence is complementary to a portion of the first target nucleotide sequence bounded by the first primer pair, wherein the first nucleotide sequence is labelled with a first quencher and a fluorophore, and wherein the first quencher is located 5' relative to the fluorophore; (ii) a polymerase extension-blocking moiety; (iii) a melt-signature region comprising a second nucleotide sequence, wherein the second nucleotide sequence is not complementary to the first target nucleotide sequence, and wherein the second nucleotide sequence includes a first non-naturally occurring nucleotide, wherein the first non-naturally occurring nucleotide is an isoC nucleotide or an isoG nucleotide; (iii) a loop region; and (iv) a melt-signature complementary region comprising a third nucleotide sequence, wherein the third nucleotide sequence is complementary to a portion of the second nucleotide sequence; and
a second probe, the second probe comprising, from 5' to 3', (i) a target-specific region comprising a first nucleotide sequence, wherein the first nucleotide sequence is complementary to a portion of the second target nucleotide sequence bounded by the second primer pair, wherein the first nucleotide sequence is labelled with a first quencher and a fluorophore, and wherein the first quencher is located 5' relative to the fluorophore; (ii) a polymerase extension-blocking moiety; (iii) a melt-signature region comprising a second nucleotide sequence, wherein the second nucleotide sequence is not complementary to the second target nucleotide sequence, and wherein the second nucleotide sequence includes a first non-naturally occurring nucleotide, wherein the first non-naturally occurring nucleotide is an isoC nucleotide or an isoG nucleotide; (iii) a loop region; and (iv) a melt-signature complementary region comprising a third nucleotide sequence, wherein the third nucleotide sequence is complementary to a portion of the second nucleotide sequence;
(b) hybridizing the melt-signature region of the first probe with the melt-signature complementary region of the first probe to form a first hairpin structure having a first melting temperature, and hybridizing the melt-signature region of the second probe with the melt-signature complementary region of the second probe to form a second hairpin structure having a second melting temperature;
(c) extending the melt-signature complementary region of the first probe along the melt-signature region of the first probe using a polymerase to form a third hairpin structure having a third melting temperature, and extending the melt-signature complementary region of the second probe along the melt-signature region of the second probe using a polymerase to form a fourth hairpin structure having a fourth melting temperature, wherein during the extending of the melt-signature complementary regions of each of the first and second probes the polymerase incorporates a second non-naturally occurring nucleotide labelled with a second quencher into each of the third and fourth hairpin structures that is complementary to the first non-naturally occurring nucleotide, and wherein the third melting temperature is higher than the first melting temperature, the fourth melting temperature is higher than the second melting temperature, and the third melting temperature is different from the fourth melting temperature;
(d) amplifying the first and second target nucleotides, if present in the sample, by polymerase chain reaction (PCR) using a polymerase having 5' to 3' nuclease activity such that during an extension step of each PCR cycle, the 5' to 3' nuclease activity of the polymerase partially cleaves the target-specific regions of the first and second probes, wherein the partial cleaving cleaves a portion of each of the first and second probes labelled with the first quencher and does not cleave a portion of the first and second probes labelled with the fluorophore;
(e) measuring a fluorescent signal at at least a first temperature that is below the third and fourth melting temperatures, measuring a fluorescent signal at at least a second temperature that is above the third melting temperature, and measuring a fluorescent signal at at least a third temperature that is above the fourth melting temperature; and
(f) detecting the presence of the first target nucleic acid if there is a change in the fluorescence signal measured below the third melting temperature as compared to the fluorescence signal measured above the third melting temperature indicative of the absence of the first quencher from the third hairpin structure as a result of the partial cleavage of the target-specific region of the first probe, and detecting the presence of the second target nucleic acid if there is a change in the fluorescence signal measured below the fourth melting temperature as compared to the fluorescence signal measured above the fourth melting temperature indicative of the absence of the first quencher from the fourth hairpin structure as a result of the partial cleavage of the target-specific region of the second probe.

10. The method of claim 9, wherein the measuring of step (e) is repeated a plurality of times during the amplifying of step (d) in order to monitor the PCR in real time.

11. The method of claim 9, wherein the measuring of step (e) is performed only after the amplifying of step (d) has reached a plateau phase.

12. The method of claim 9, further comprising partitioning the sample into a plurality of partitions such that, if the first and/or second target nucleic acids are present in the sample, at least one partition of the plurality of partitions will not contain a first target nucleic acid and at least one partition of the plurality of partitions will not contain a first target nucleic acid, wherein the partitioning of the sample is performed prior to performing at least step (d).

13. The method of claim 12, wherein the partitioning of the sample is performed prior to performing any of steps (b) through (f).

* * * * *